United States Patent [19]
Kawauchi et al.

[11] Patent Number: 5,532,349
[45] Date of Patent: Jul. 2, 1996

[54] PROCESS FOR PRODUCING 1-(2'-DEOXY-β-D-ERYTHRO-PENTOFURANOSYL)-5-TRIFLUOROMETHYLURACIL DERIVATIVES

[75] Inventors: Nobuya Kawauchi, Yokohama; Nobuyuki Fukazawa, Mobara; Hiroki Ishibashi, Mobara; Kengo Otsuka, Mobara, all of Japan

[73] Assignee: Mitsui Toatsu Chemicals, Inc., Tokyo, Japan

[21] Appl. No.: 275,455

[22] Filed: Jul. 15, 1994

[30] Foreign Application Priority Data

Jul. 20, 1993 [JP] Japan .................................. 5-179415
Jul. 20, 1993 [JP] Japan .................................. 5-179416

[51] Int. Cl.⁶ ........................ C09H 19/073; A01K 31/70
[52] U.S. Cl. ........................ 536/55.3; 536/28.54
[58] Field of Search ................. 536/124, 28.54, 536/55.3

[56] References Cited

U.S. PATENT DOCUMENTS 3,748,320  7/1973  Vorbruggen et al. ............... 536/28.54

FOREIGN PATENT DOCUMENTS 0389110  9/1990  European Pat. Off.
60-23397  2/1985  Japan.

OTHER PUBLICATIONS

Kawakami et al, Heterocycles, vol. 31, No. 3, pp. 569–574 (1990).

March, Jerry, Advanced Organic Chemistry, Third Edition, John Wiley & Sons, New York: 1985, p. 1092.

*Primary Examiner*—Gary L. Kunz

*Attorney, Agent, or Firm*—Birch, Stewart, Kolasch & Birch

[57] ABSTRACT

A process for producing 1-(2'-deoxy-B-D-erythropentofuranosyl)-5-trifluoromethyluracil derivatives having the formula as shown below:

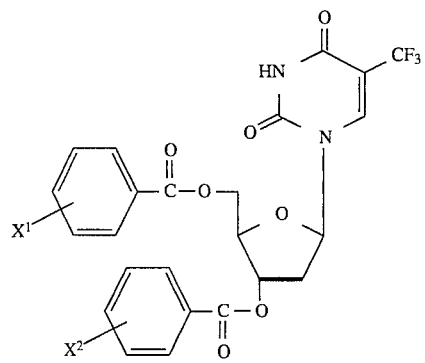

wherein $X^1$ and $X^2$ are independently hydrogen or halogen, comprising:
(a) reacting 5-trifluoromethyl-5,6-dihydrouracil with alkylsulfoxide in the presence of a halogen and and acid to obtain 5-trifluoromethyluracil;
(b) reacting the obtained 5-trifluoromethyluracil with a silylating agent to obtain 5-trifluoromethyl-2,4-bis(trimethylsilyloxy)uracil; and
(c) reacting the obtained 5-trifluoromethyl-2,4-bis(trimethylsilyloxy)uracil with a protected 2-deoxyalpha-D-erthro-pentofuranosyl)halide derivative in chloroform solvent in the presence of fluoride ion and in the presence of a copper compound as a catalyst.

The resulting, deblocked nucleosides are useful as antiviral and antitumor agents.

8 Claims, No Drawings

PROCESS FOR PRODUCING 1-(2'-DEOXY-β-D-ERYTHRO-PENTOFURANOSYL)-5-TRIFLUOROMETHYLURACIL DERIVATIVES

BACKGROUND OF THE INVENTION

I. Field of the Invention

The present invention relates a process for producing 1-(2'-deoxy-β-D-erythro-pentofuranosyl)-5-trifluoromethyluracil derivatives having anti-tumor and anti-viral activities, as well as to a process for producing an intermediate thereof.

II. Description of the Related Art 1-(2'-deoxy-β-D-erythro-pentofuranosyl)-5-trifluoromethyluracil derivatives (trifluorothymidine derivatives) are compounds which have long been drawing attention because of their relationships between uridine or thymidine. Since they have anti-tumor and anti-viral activities, they are important as pharmaceuticals or intermediates for producing the pharmaceuticals, so that processes for producing them have been well studied. It is well known in the field of synthetic organic chemistry in this area that the processes for producing the derivatives largely vary depending on the type of the base in the nucleoside, so that a suitable production process should be studied for each type of the bases. For example, as described in Nucleic Acids Research 12, 6827 (1984) or in Nucleosides & Nucleotides, 8, 549 (1989), bases of nucleic acids, such as uracil, fluorouracil, thymine and trifluorothymine have largely different properties because of the difference in the substituent group on 5-position. Therefore, a production process by utilizing glycosylation must be developed for each of the above-mentioned bases. Especially, 5-trifluoromethyluridine has chemical properties largely different from those of uridine and thymidine because of the influence by the trifluoromethyl group, so that 5-trifluoromethyluridine cannot be produced well by a production process analogous to the process for producing uridine or thymidine. Further, if a compound having 2'-deoxy structure in the sugar moiety is produced by a conventional process, the selectivity of α and β isomers is low, so that it is difficult to selectively obtain the necessary β isomer alone.

Known processes for producing 1-(2'-deoxy-β-D-erythro-pentofuranosyl)-5-trifluoromethyluracil derivatives include:

(1) A process in which the base of thymidine is exchanged with 5-trifluoromethyluracil by nucleoside-2'-deoxyribose transferase or the like (M. G. Stout et al., Methods Carbhydro Res., 7, 19 (1976);

(2) A process in which the halogen atom at 5-position of a 1-(2'-deoxy-β-D-erythro-pentofuranosyl)-5-halouracil derivative is reacted with trifluoromethylcopper (Y. Kobayashi, et al., J. C. S. Perkin Trans I, 2755 (1980));

(3) A process in which a thymidine derivative and trifluoroacetic acid are subjected to electrolysis reaction (L. Hein, et al., DE 119423 (1976));

(4) A process in which 5-trifluoromethyl-2,4-bistrimethylsilyloxy)pyrimidine and methyl 2-deoxy-D-erhythro-pentofuranoside derivative are reacted in the presence of an acid catalyst (Japanese Laid-open PCT Application (Kohyo) No. 62-500239)); and (5) A process in which 5-trifluoromethyl-2,4-bis(trimethylsilyloxy)pyrimidine and 3,5-di-O-(p-chlorobenzoyl)-2-deoxy-α-D-erythro-pentofuranosyl chloride are reacted in the presence of zinc chloride catalyst (Japanese Laid-open Patent Application (Kokai) No. 2-289595, Heterocycles, 31, 569 (1990)).

However, the above-mentioned process (1) has a drawback in that isolation of the desired product from the reaction system is difficult so that it is difficult to produce the desired product in a large scale. The process (2) has a drawback in that a reaction intermediate is very sensitive to air, so that it is difficult to set reaction conditions and the yield is low. The process (3) has a drawback in that both the yield and electric efficiency are low, and an equipment for electrolysis which can withstand trifluoroacetic acid is necessary. The process (4) has a drawback in that the desired product is obtained as a racemate which is difficult to resolve, so that isolation yield of the desired β isomer is very low. The process (5) has a drawback in that expensive 5-trifluoromethyl-2,4-bis(trimethylsilyloxy)pyrimidine is required in a large amount. Further, in this process, it is necessary to employ zinc chloride which is hygroscopic and insoluble in solvents, and so has poor ease of handling as a catalyst, so that the reproducibility of the process is low and it is difficult to carry out the process in an industrial scale. Still further, if the expensive 5-trifluoromethyl-2,4-bis(trimethylsilyloxy)pyrimidine is used in an amount smaller than the equimolar amount, the selectivity to β isomer is extremely decreased, so that the yield of the desired β isomer is largely reduced.

Thus, none of the conventional processes is suited as a process for producing 1-(2'-deoxy-β-D-erythropentofuranosyl)- 5-trifluoromethyluracil derivatives which are important as pharmaceuticals or intermediates thereof in a large scale at a low cost with certainty. Thus, an improved process for producing 1-(2'-deoxy-β-D-erythropentofuranosyl)- 5-trifluoromethyluracil derivatives is demanded.

On the other hand, trifluoromethyluracil is a compound which has been drawing attention because of the relationship between uracil or thymine that is a base of nucleic acid. Especially, processes for producing trifluorothymidine derivatives which are used as anti-cancer agents or anti-viral agents because of their specific physical properties and actions, or as important intermediates for the production of pharmaceuticals such as 1-(2'-deoxy-β-D-erythro-pentofuranosyl)-5-trifluoromethyluracil derivatives, have been intensively studied. Conventional processes for producing 5-trifluoromethyluracil include:

(1) A process in which 5-hydroxycarbonyluracil is reacted with $SF_4$ (M. P. Merite, et al., J. Pharm. Sci., 2, 508 (1963));

(2) A process in which 5-iodouracil is reacted with trifluoromethylcopper (Y. Kobayashi et al., J. C. S. Perkin I, 2755 (1980));

(3) A process in which uracil and trifluoroacetic acid are subjected to electrolysis reaction (L. Hein, D. Cech, Z. Chem., 17,415 (1977));

(4) A process in which 5-trifluoromethyl-5,6-dihydrouracil is reacted with bromine (C. Heiderberger, et al., J. Med. Chem., 7, 1 (1964); Japanese Laid-open Patent Application (Kokai) No. 58-174371); and (5) A process in which 5-trifluoromethyl-5,6-dihydrouracil is reacted with cupric halide (Japanese Laid-open Patent Application (Kokai) No. 60-94971).

However, the above-mentioned process (1) has a drawback in that dangerous $SF_4$ having high toxicity must be used. The process (2) has a drawback in that a reaction intermediate is very sensitive to air, so that it is difficult to set reaction conditions and the yield is low. The process (3)

has a drawback in that both the yield and electric efficiency are low, and an equipment for electrolysis, which can withstand trifluoroacetic acid is necessary. The process (4) has a drawback in that more than twice the stoichiometric amount of bromine is required and the yield is low. The process (5) has a drawback in that a large amount of residue containing copper salt is generated after the reaction, so that there are problems in ease of operation and disposal of the copper salt-containing residue.

Thus, none of the conventional processes for producing trifluoromethyluracil is a process by which the desired product is produced at a low cost with certainty. Thus, an improved process is demanded.

SUMMARY OF THE INVENTION

Accordingly, an object of the present invention is to provide a process for producing 1-(2'-deoxy-β-D-erythro-pentofuranosyl)-5-trifluoromethyluracil derivatives by which the desired product can be produced easily at a low cost.

Another object of the present invention is to provide a process for producing trifluoromethyluracil by which the desired product can be produced easily at a low cost.

The present inventors discovered a novel dehydrogenating reaction of 5-trifluoromethyl-5,6-dihydrouracil and discovered that in the glycosylation reaction of 5-trifluoromethyl-2,4-bis(trimethylsilyloxy)pyrimidine using a copper compound as a catalyst, by using chloroform as the solvent and by carrying out the reaction in the presence of fluoride ion, surprisingly, the reaction proceeds with very high selectivity and high yield, and satisfactory results can be obtained even if stoichiometric amounts of the reactants are used, which is very advantageous from the economical viewpoint.

That is, the present invention provides a process for producing 1-(2'-deoxy-β-D-erythro-pentofuranosyl)-5-trifluoromethyluracil derivative of the formula (3)

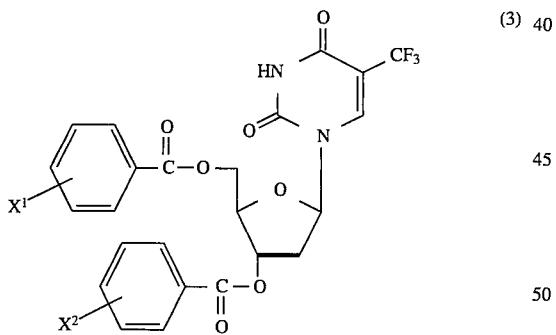

comprising the steps of:

(a) reacting 5-trifluoromethyl-5,6-dihydrouracil with alkylsulfoxide in the presence of a halogen and an acid catalyst to obtain 5-trifluoromethyluracil;

(b) reacting the obtained 5-trifluoromethyluracil with a silylating agent to obtain 5-trifluoromethyl-2,4-bis(trimethylsilyloxy)pyrimidine of the formula (1)

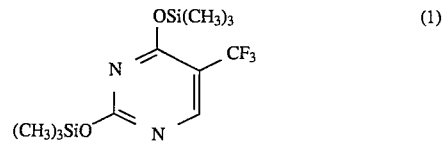

and (c) reacting the obtained 5-trifluoromethyl-2,4-bis(trimethylsilyloxy)pyrimidine with 2-deoxy-α-D-erythro-pentofuranosyl halide derivative of the formula (2)

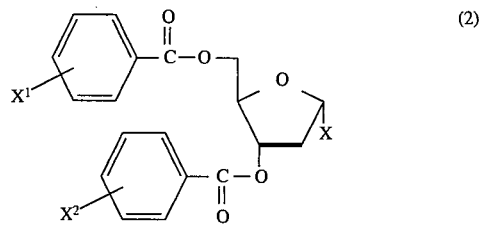

(wherein X represents a halogen atom, preferably chlorine atom, preferably chlorine atom, and $X^1$ and $X^2$, the same or different, represent hydrogen or a halogen atom, preferably hydrogen or chlorine atom) in chloroform solvent in the presence of fluoride ion and in the presence of a copper compound as a catalyst.

By the process of the present invention, 1-(2'-deoxy-β-D-erythro-pentofuranosyl)-5-trifluoromethyluracil derivative of the formula (3) may be produced easily at a low cost with high selectivity to β isomer.

DETAILED DESCRIPTION OF THE PREFERRED EMBODIMENTS

The process according to the present invention is expressed by the following reaction equation:

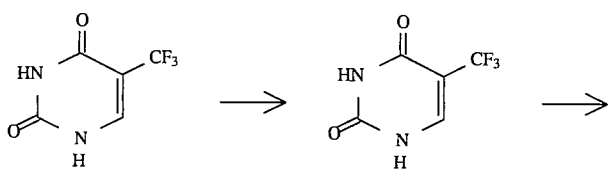

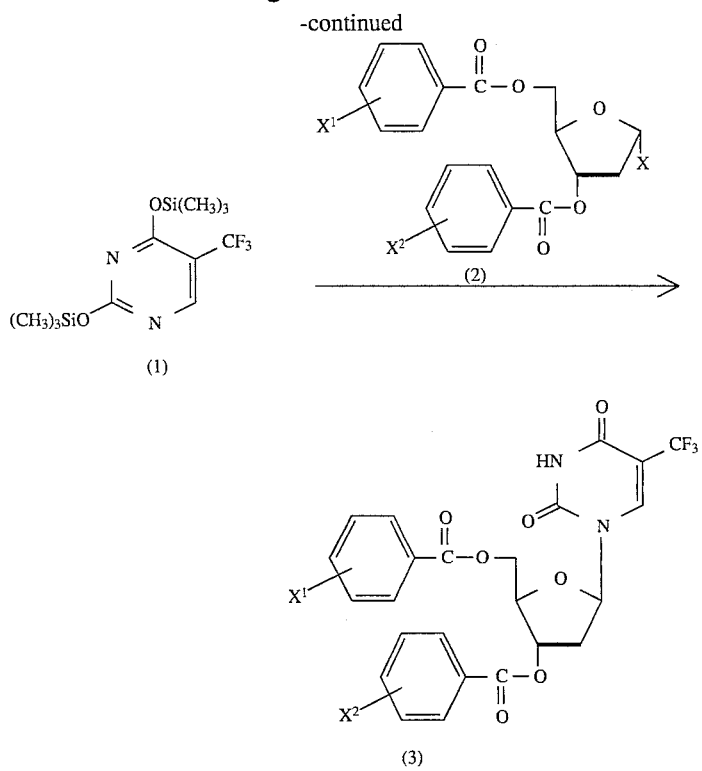

Each step will now be described in detail.

Step (a)

In this step, 5-trifluoromethyl-5,6-dihydrouracil is reacted with alkylsulfoxide in the presence of a halogen and an acid catalyst. 5-trifluoromethyl-5,6-dihydrouracil employed as a starting material in this step is a well-known compound which can be easily obtained by reacting trifluoromethacrylic acid and urea (e.g., T. Fuchigami et al., Synthesis, 766 (1984)).

The alkylsulfoxide used in this step is preferably expressed by the formula $R^1SOR^2$ (wherein $R^1$ and $R^2$, the same or different, represent $C_1$–$C_4$ alkyl), although the alkylsulfoxide which may be employed in this step is not restricted thereto. Preferred examples of the alkylsulfoxide include dimethylsulfoxide, diethylsulfoxide and the like. Alkylsulfoxide may preferably be used in an amount of not less than one equivalent, more preferably 2 to 10 equivalents, with respect to 5-trifluoromethyl-5,6-dihydrouracil.

Preferred examples of the halogen which may be employed in this step include $I_2$, $Br_2$, ClI and the like. Among these, $I_2$ is best preferred. The halogen may preferably be used in an amount of 0.01 to 10 equivalents, more preferably 0.07 to 0.5 equivalents, with respect to 5-trifluoromethyl-5,6-dihydrouracil.

Examples of the acid catalyst employed include organic acids such as trifluoroacetic acid, camphor sulfonic acid, p-toluenesulfonic acid and trimethylsilyl chloride; and inorganic acids such as phosphorus pentoxide, sulfuric acid and hydrochloric acid. Among these, sulfuric acid is best preferred. The acid catalyst may be used in an amount of preferably 0.01 to 1 equivalent, more preferably 0.07 to 0.5 equivalents with respect to 5-trifluoromethyl-5,6-dihydrouracil.

The reaction may be carried out either in the presence or absence of a solvent. Any solvent which does not adversely affect the reaction may be employed. Specific examples of the solvent include aprotic solvents such as chloroform, benzene, toluene, 1,2-dimethoxyethane, and dimethylformamide. To carry out the reaction in the absence of a solvent or in dimethylformamide as a solvent is preferred.

The reaction temperature may be from room temperature to the boiling point of the solvent, preferably 90°–150° C. The reaction time may usually be 0.5–72 hours.

Step (b)

In this step, the obtained 5-trifluoromethyluracil is reacted with a silylating agent to obtain 5-trifluoromethyl- 2,4-bis(trimethylsilyloxy)pyrimidine of the above-described formula (1). This step can be easily carried out according to a known process by reacting a conventional silylation agent and 5-trifluoromethyluracil (T. A. Khawaja et al, J. Med. Chem., 12, 543 (1969)).

As the silylating agent, trimethylchlorosilane, trimethylsilyltriflate, bistrimethylsilylacetamide, hexamethyldisilazane and the like may be used in the presence of an acid catalyst, base catalyst or in the absence of a catalyst. Examples of the acid catalysts include organic acids such as p-toluenesulfonilc acid, trimethylsilyl chloride and trimethylsilyltriflate; and inorganic acids such as sulfuric acid and ammonium bisulfate. Examples of the base catalysts include organic bases such as trimethylamine, pyridine and 4-dimethylaminopyridine; and inorganic bases such as sodium hydride and ammonia. It is preferred to use hexamethyldisilazane in the presence of trimethylchlorosilane. The silylating agent may preferably be used in an amount of not less than 2 equivalents, more preferably 2–15 equivalents, with respect to 5-trifluoromethyluracil. In cases where a catalyst is used, the catalyst may preferably be used in an amount of 0.01 to 1 equivalent, more preferably 0.01 to 0.5 equivalents, with respect to 5-trifluoromethyluracil.

This reaction may be carried out in the presence or absence of a solvent. Any solvent which does not adversely affect the reaction may be employed. Specific examples of the solvent include aprotic solvents such as tetrahydrofuran, 1,4-dioxane, chloroform, methylene chloride, benzene, toluene, dimethylformamide, and dimethylacetamide. To carry out the reaction in the absence of a solvent or in tetrahydrofuran as a solvent is preferred.

The reaction temperature may be from room temperature to the boiling point of the solvent, preferably 25°–140° C. The reaction time may usually be 0.5–72 hours.

Step (c)

In this step, the obtained 5-trifluoromethyl-2,4-bis(trimethylsilyloxy)pyrimidine is reacted with 2-deoxy-α-D-erythro-pentofuranosyl halide derivative of the formula (2) in chloroform solvent in the presence of fluoride ion and in the presence of a copper compound as a catalyst. A representative of one of the starting materials, 3,5-di-O-(p-chlorobenzoyl)-2-deoxy-α-D-erythro-pentofuranosyl chloride can be synthesized by known methods from 2-deoxyribose which is readily available (e.g., J. J. Fox et al., J. Am. Chem. Soc., 83, 4066 (1961)).

In this reaction, 5-trifluoromethyl-2,4-bis(trimethylsilyloxy)pyrimidine is used in an amount of 0.5 to 2 equivalents, more preferably from the economical view point, 0.5 to 1 equivalent, with respect to 3,5-di-O-(p-chlorobenzoyl)-2-deoxy-α-D-erythropentofuranosyl chloride.

As the copper compound used as a catalyst, those having low hygroscopisity and good ease of handling, such as cupric chloride and copper fluoride may be employed. The copper compound may preferably be used in an amount of 0.01 to 1 equivalent, more preferably 0.05 to 0.5 equivalents, with respect to 3,5-di-O-(p-chlorobenzoyl)-2-deoxy-α-D-erythro-pentofuranosyl chloride.

The presence of fluoride ion can be attained by adding a fluoride to the reaction system. When the copper compound used as a catalyst is copper fluoride mentioned above, the fluoride ion is provided by this compound. In cases where the copper compound does not contain fluorine, a fluoride such as cesium fluoride, potassium fluoride or the like may be added. Although the amount of the fluoride ion is not restricted, usually 0.05 to 3 equivalents, preferably 0.1 to 2 equivalents of fluoride ion is employed with respect to the copper compound.

The solvent employed in this reaction is chloroform. If other solvents are used, the selectivity to β isomer is reduced.

The reaction temperature may be from –40° C. to the boiling point of the solvent, preferably –10 to room temperature. The reaction time may usually be 0.5–48 hours.

A process for producing 3′,5′-di-substituted-2′-deoxy-5-fluorouridine by glycosylation in the presence of a fluoride is disclosed in Japanese Laid-open Patent Application (Kokai) No. 60-23397. However, this reference is totally silent about trifluoromethyluridines to which the present invention pertains. Further, as is evident from Comparative Example 2 described below, if a solvent other than chloroform is used, both of the selectivity and yield are unsatisfactory. Further, as described in Nucleosides & Nucleotides 8549 (1989) or the like, the reactivity of the glycosylation reaction using a copper compound largely varies depending on the halogen ion employed. Thus, the advantageous effect obtained by carrying out the glycosylation reaction in the presence of a copper compound and fluoride ion in chloroform solvent is specific to trifluoromethyluridines, which is an important characteristic feature of the present invention.

As will be apparent from the examples described below in detail, the above-mentioned process according to the present invention can be carried out at a low cost and is excellent in ease of operation and selectivity to β isomer. Thus, the process according to the present invention is much superior to the conventional processes as an industrial process from the economical viewpoint, and has a technical originality.

1-[3′,5′-di-O-(p-chlorobenzoyl)-2′-deoxy-β-D-erythropentofuranosyl]-5-trifluoromethyluracil which can be obtained by the process according to the present invention can be easily converted to 1-(2′-deoxy-β-D-erythropentofuranosyl)- 5-trifluoromethyluracil (trifluorothymidine) important as a pharmaceutical or an intermediate for producing a pharmaceutical by a process well-known in the art (for example, alkaline hydrolysis or the like).

The present invention will now be described in more detail by way of examples thereof. It should be noted that the examples are presented for the illustration purpose only and should not be interpreted in any restrictive way.

Reference Example 1

Synthesis of 5-trifluoromethyl-5,6-dihydrouracil

In 160 ml of acetic anhydride, 13.5 g of urea was suspended and 30 g of trifluoromethacrylic acid was added to the suspension. The resulting mixture was allowed to react at 100° C. for 1 hour and the reaction mixture was concentrated under reduced pressure. The obtained oil was crystallized from 150 ml of water and then recrystallized from 150 ml of water to obtain 25.9 g of 5-trifluoromethyl-5,6-dihydrouracil.

m.p.: 203°–205° C.

EXAMPLE 1

Synthesis of 5-trifluoromethyluracil

In 88.7 ml of dimethylsulfoxide, 25.2 g of 5-trifluoromethyl-5,6-dihydrouracil was dissolved and 3.47 g of iodine and 0.76 ml of concentrated sulfuric acid were added to the solution to obtain a uniform solution. The obtained solution was stirred at 140° C. for 6 hours, and then cooled to room temperature, followed by adding 150 g of 3% aqueous sodium sulfite solution to reduce iodine. The resulting mixture was concentrated under reduced pressure. After adding water to the residue, the residue was extracted three times with ethyl acetate. The ethyl acetate layer was concentrated and the residue was recrystallized from 1.00 ml of water to obtain 21.9 g (88%) of 5-trifluoromethyluracil as white needle-shaped crystals.

m.p.: 239°–241° C. NMR: identical to that reported in references

EXAMPLE 2

Synthesis of 5-trifluoromethyluracil

In 24.7 ml of dimethylformamide, 10 g of 5-trifluoromethyl-5,6-dihydrouracil is dissolved, and 12.8 g of dimethylsulfoxide, 1.4 g of iodine and 0.54 g of concentrated sulfuric acid were added to obtain a uniform solution. The obtained solution was stirred at 117° C. for 9 hours. The resultant was cooled to room temperature and 70 g of 3% aqueous sodium sulfite was added to reduce iodine. The resulting mixture was concentrated under reduced pressure. Water was added to the residue and the residue was extracted three times with ethyl acetate. The ethyl acetate layer was concentrated and the residue was recrystallized from 40 ml of water to obtain 7.2 g (73%) of 5-trifluoromethyluracil in the form of white needle-shaped crystals.

EXAMPLE 3

Synthesis of 5-trifluoromethyluracil

In 73.9 ml of dimethylsulfoxide, 25.2 g of 5-trifluoromethyl- 5,6-dihydrouracil was dissolved, and 2.44 g of iodine and 0.54 ml of concentrated sulfuric acid were added to obtain a uniform solution. The solution was stirred at 150° C. for 8 hours, and the resultant was cooled to room temperature, followed by adding 120 g of 3% aqueous sodium sulfite solution to reduce iodine. The resulting solution was concentrated under reduced pressure. After adding water to the obtained residue, the residue was extracted three times with ethyl acetate. The ethyl acetate layer was dried over anhydrous sodium sulfate and the obtained residue was crystallized from chloroform, and then recrystallized from 100 ml of water to obtain 14.8 g of 5-trifluoromethyluracil in the form of white needle-shaped crystals.

EXAMPLE 4

Synthesis of 5-trifluoromethyluracil

In 93.6 ml of dimethylsulfoxide, 17.2 g of iodine and 3.6 ml of concentrated sulfuric acid were dissolved, and 25.2 g of 5-trifluoromethyl-5,6-dihydrouracil was added to obtain a uniform solution. The solution was stirred at 140° C. for 4 hours. The resulting mixture was allowed to cool to room temperature and 500 g of 3% aqueous sodium sulfite solution was added to reduce the iodine. The resultant was concentrated under reduced pressure and the obtained residue was dissolved in 150 ml of hot water. The resulting mixture was refrigerated for 2 days and the precipitated white needle-shaped crystals were collected by filtration and dried to obtain 15.1 g of 5-trifluoromethyluracil.

Reference Example 2

Synthesis of methyl 2-deoxy-D-erythro-pentofuranoside

In 1.1 liters of methanol, 52 g of 2-deoxy-D-erythropentose was dissolved, and 3.8 ml of 1M hydrochloric acid solution in methanol was added at room temperature, followed by stirring the resulting solution at room temperature for 1 hour. To the reaction mixture, 1 g of sodium hydrogen carbonate was added and the resultant was concentrated after confirming that the solution was weakly basic. To the residue, 100 ml of toluene and 100 ml of pyridine were added to dissolve the residue and the resultant was concentrated. This operation was repeated totally twice to completely remove methanol. The thus obtained crude methyl 2-deoxy-α-D-erythro-pentofuranoside was used in the subsequent step without purification.

Reference Example 3

Synthesis of methyl 3,5-di-O-(p-chlorobenzoyl)-2-deoxy-α-D-erythropentofuranoside The thus obtained crude product was dissolved in 260 ml of pyridine and the solution was cooled in ice. To the resulting solution, 150 g of p-chlorobenzoyl chloride was added dropwise over 1 hour while keeping the reaction temperature not higher than 30° C. After leaving the resulting solution to stand overnight at room temperature, 10 ml of methanol was added and the resultant was stirred at room temperature for 2 hours. The reaction mixture was then poured into 1 liter of water and the mixture was extracted twice with 500 ml of isopropyl ether. The extract was washed three times with 100 ml of 10% sulfuric acid and the resultant was dried over magnesium sulfate. The obtained crude product was used in the subsequent reaction as the solution in isopropyl ether.

Reference Example 4

Synthesis of 3,5-di-O-(p-chlorobenzoyl]-2-deoxy-α-D-erythro-pentofuranosyl chloride One tenth (1/10) volume of the thus obtained solution in isopropyl ether was taken and cooled to 0° C. Into this solution, 20 g of hydrochloric acid gas was blown over 40 minutes at a rate at which the temperature of the reaction mixture is kept at 8°–13° C. After stirring the mixture for another 1 hour at this temperature, the generated desired product was collected by filtration. The obtained crystals were washed with 20 ml of cold isopropyl ether and then with 20 ml of hexane, and the resultant was dried at room temperature in vacuum drier for 5 hours. Yield: 11.75 g (70.5% based on 2-deoxy-α-D-erythro-pentose).

The thus obtained compound may be hereinafter referred to as "Compound (II)".

EXAMPLE 5

Synthesis of 5-trifluoromethyl-2,4-bis(trimethylsilyloxy)pyrimidine

In 50 ml of hexamethyldisilazane, 6.16 g of 5-trifluoromethyluracil was suspended and then 0.22 ml of trimethylchlorosilane was added to the suspension, followed by heating the resulting mixture to reflux for 5 hours. After the reaction, the excess hexamethyldisilazane was removed by evaporation and the resultant was distilled in vacuum. All of the fractions of distillate obtained at about 60° C. under 1 mmHg were collected. Yield: 10.3 g The thus obtained compound may be hereinafter referred to as "Compound (I)".

EXAMPLE 6

Synthesis of 1-[3',5'-di-O-(p-chlorobenzoyl)-2'-deoxy-β-D-erythropentofuranosyl]-5-trifluoromethyluracil In 8 ml of chloroform, 869 mg of 3,5-di-(p-chlorobenzoyl)- 2-deoxy-α-D-erythro-pentofuranosyl chloride and 656 mg of 5-trifluoromethyl-2,4-bis(trimethylsilyloxy)pyrimidine were dissolved. To this solution, 21 mg of copper fluoride was added at room temperature and the resulting mixture was stirred for 24 hours at room temperature. After the reaction, 1N hydrochloric acid was added and the mixture was separated into aqueous and organic layers. The organic layer was washed with water and dried over magnesium sulfate. By concentrating the organic layer, 1-[3',5'-di-O-(p-chlorobenzoyl)-2'-deoxy-D-erythropentofuranosyl] -5-trifluoromethyluracil containing α and β isomers at a ratio of 1:11 was obtained with a yield of 98%. By recrystallizing the obtained product from ethanol, pure 1-[3',5'-di-O-(p-chlorobenzoyl)-2'-deoxy-β-D-erythropentofuranosyl]-5-trifluoromethyluracil was obtained.

Yield: 997 mg (86%) NMR, m.p.: identical to those reported in references

Comparative Example 1

Synthesis of 1-[3',5'-di-O-(p-chlorobenzoyl)-2'-deoxy-β-D-erythropentofuranosyl]-5-trifluoromethyluracil In accordance with the process described in Japanese Laid-open Patent Application (Kokai) No. 2-289595, Compounds (I) and (II) were reacted at a molar ratio of 1:1 using zinc chloride as a catalyst as follows:

In 6 ml of chloroform, 616 mg of 3,5-di-O-(p-chlorobenzoyl)- 2-deoxy-α-D-erythro-pentofuranosyl chloride and 465 mg of 5-trifluoromethyl-2,4-bis(trimethylsilyloxy)pyrimidine were dissolved. To this solution, 19 mg of zinc chloride was added at room temperature and the resulting mixture was stirred at room temperature for 24 hours. After the reaction, aqueous sodium hydrogen carbonate solution was added and the resultant was separated into aqueous and organic layers. The organic layer was washed with water and dried over magnesium sulfate, followed by concentration of the organic layer to obtain 1-[3',5'-di-O-(p-chlorobenzoyl)-2'-deoxy-D-erythro-pentofuranosyl]-5-trifluoromethyluracil containing α and β isomers at a ratio of 1:3 was obtained with a yield of 77%. The obtained product was recrystallized from ethanol to obtain pure 1-[3',5'-di-O-(p-chlorobenzoyl)-2'-deoxy-βD-erythro-pentofuranosyl]-5-trifluoromethyluracil.

Yield: 288 mg (35%) NMR, m.p.: identical to those reported in references

Comparative Example 2

Synthesis of 1-[3',5'-di-O-(p-chlorobenzoyl)-2'-deoxy-β-D-erythropentofuranosyl]-5-trifluoromethyluracil In accordance with the process described in Japanese Laid-open Patent Application (Kokai) No. 60-23397, Compounds (I) and (II) were reacted at a molar ratio of 1:1 employing copper fluoride as a catalyst and 1,2-dichloroethane as a solvent as follows:

In 6 ml of 1,2-dichloroethane, 530 mg of 3,5-di-O-(p-chlorobenzoyl)-2-deoxy-α-D-erythropentofuranosyl chloride and 400 mg of 5-trifluoromethyl-2,4-bis(trimethylsilyloxy)pyrimidine were dissolved. To this solution, 12 mg of copper fluoride was added at room temperature and the resulting mixture was stirred at room temperature for 24 hours. After the reaction, 1N hydrochloric acid was added and the mixture was separated into aqueous and organic layers. The organic layer was washed with water and dried over magnesium sulfate. The organic layer was concentrated to obtain 1-[3',5'-di-O-(p-chlorobenzoyl)-2'-deoxy-D-erythropentofuranosyl]-5-trifluoromethyluracil containing α and β isomers at a ratio of 1:1.4 with a yield of 96%. The obtained product was recrystallized from ethanol to obtain pure 1-[3',5'-di-O-(p-chlorobenzoyl)-2'-deoxy-β-D-erythropentofuranosyl]-5-trifluoromethyluracil.

Yield: 106 mg (15%) NMR, m.p.: identical to those reported in references

Comparative Example 3

Synthesis of 1-[3',5'-di-O-(p-chlorobenzoyl)-2'-deoxy-β-D-erythropentofuranosyl]-5-trifluoromethyluracil The reaction between Compounds (I) and (II) in the presence of copper chloride as a catalyst but in the absence of fluoride ion was carried out as follows:

In 150 ml of chloroform, 7.9 g of 3,5-di-O-(p-chlorobenzoyl)-2-deoxy-α-D-erythro-pentofuranosyl chloride and 5.89 g of 5-trifluoromethyl-2,4-bis(trimethylsilyloxy)pyrimidine were dissolved. The solution was cooled to 0° C. and 0.25 g of copper chloride was added to the solution. After allowing the solution to react at 0° C. for 10 hours, the reaction mixture was poured into 1N hydrochloric acid and the mixture was separated into aqueous and organic layers. The organic layer was washed with water and then with aqueous saturated sodium hydrogen carbonate solution, and dried over magnesium sulfate. By concentrating the resultant, a colorless transparent glassy product was obtained. The obtained product was recrystallized from ethanol to obtain 1-[3',5'-di-O-(p-chlorobenzoyl)-2'-deoxy-β-D-erythropentofuranosyl]-5-trifluoromethyluracil.

Yield: 3.2 g (30%) NMR, m.p.: identical to those reported in references

EXAMPLES 7–10

The procedure as in Example 6 was repeated except that the molar ratio of Compound (I) to Compound (II) was 1.2:1.0–0.9:1.0, and the amount of the copper fluoride was 1.0–0.1 equivalent.

After the reaction, the reaction solution was treated as in Example 6, and the yield of the total of α and β isomers based on Compound (I), isolation yield of the β isomer alone and the selectivity in terms of the molar ratio of β isomer:β isomer were determined.

The results are shown in Table 1.

TABLE 1

|  | Molar Ratio (I):(II) | Amount of Catalyst | α isomer + β isomer (%) | Isolation Yield β isomer (%) | Selectivity α isomer:β isomer |
| --- | --- | --- | --- | --- | --- |
| Example 6 | 1.0:1.0 | 0.1 | 98 | 86 | 1:11 |
| Example 7 | 1.2:1.0 | 0.1 | 82 | 70 | 1:15 |
| Example 8 | 0.9:1.0 | 0.1 | 98 | 81 | 1:8 |
| Example 9 | 0.9:1.0 | 0.5 | 98 | 81 | 1:8 |
| Example 10 | 0.9:1.0 | 1.0 | 98 | 81 | 1:8 |
| Comparative Example 1 | 1.0:1.0 | 0.1 | 77 | 35 | 1:3 |
| Comparative Example 2 | 1.0:1.0 | 0.1 | 96 | 15 | 1:1.4 |
| Comparative Example 3 | 1.0:1.0 | 0.1 | 85 | 30 | 1:2 |

Example 11

Synthesis of 1-[3',5'-di-O-(p-chlorobenzoyl)-2'-deoxy-β-D-erythropentofuranosyl]-5-trifluoromethyluracil In 150 ml of chloroform, 7.9 g of 3,5-di-O-(p-chlorobenzoyl)-2-deoxy-α-D-erythro-pentofuranosyl chloride and 5.89 g of 5-trifluoromethyl-2,4-bis(trimethylsilyloxy)pyrimidine were dissolved. The obtained solution was cooled to −5° C. and 2.5 g of cesium fluoride and 0.72 g of cupric chloride were added to the solution. After allowing the reaction at −5° C. for 4 hours, the reaction solution was washed with 1N hydrochloric acid, with water and then with aqueous saturated sodium hydrogen carbonate solution, followed by drying over magnesium sulfate. The resultant was concentrated to obtain a colorless transparent hard glassy product. The obtained product was recrystallized from 15 ml of ethanol to obtain 1-[3',5'-di-O-(p-chlorobenzoyl)-2'-deoxy-β-D-erythro-pentofuranosyl]-5-trifluoromethyluracil.

Yield: 8.4 g (80%) NMR, m.p.: identical to those reported in references From the above-described Examples and Comparative Examples, the advantageous effects of the present invention are evident.

More particularly, in Example 6 wherein expensive 5-trifluoromethyl-2,4-bis(trimethylsilyloxy)pyrimidine was used in an amount of one equivalent, the yield was as high as 98% and the α:β selectivity was as high as 1:11. In contrast, in the process according to Japanese Laid-open Patent Application (Kokai) No. 2-289595 described in Comparative Example 1, the yield was 77% and the α:β selectivity was 1:3. Thus, the advantageous effects of the present invention over the conventional process is evident. Further, by the process according to Japanese Laid-open Patent Application (Kokai) No. 60-23397 described in Comparative Example 2, the α:β selectivity was 1:1.4 so that the isolation yield of the necessary β isomer was as low as 15%. Thus, the advantage of employing chloroform as the solvent is suggested. Further, as shown in Comparative Example 3, in the absence of fluoride ion, α:β selectivity was as low as 1:2. Thus, the advantage of employing fluoride ion is suggested.

We claim:

1. A process for producing 1-(2'-deoxy-β-D-erythro-pentofuranosyl)-5-trifluoromethyluracil derivative of the formula (3)

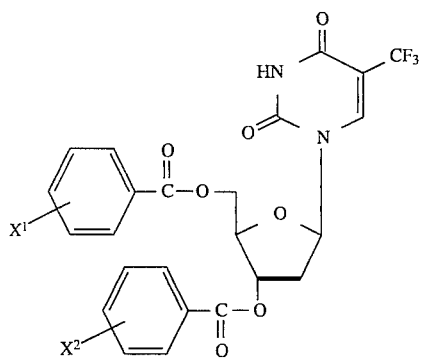

comprising the steps of:
(a) reacting 5-trifluoromethyl-5,6-dihydrouracil with alkylsulfoxide in the presence of a halogen and an acid catalyst to obtain 5-trifluoromethyluracil;
(b) reacting the obtained 5-trifluoromethyluracil with a silylating agent to obtain 5-trifluoromethyl-2,4-bis(trimethylsilyloxy)pyrimidine of the formula (1)

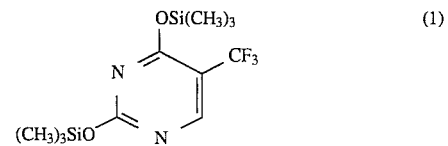

and
(c) reacting the obtained 5-trifluoromethyl-2,4-bis(trimethylsilyloxy)pyrimidine with 2-deoxy-α-D-erythro-pentofuranosyl halide derivative of the formula (2)

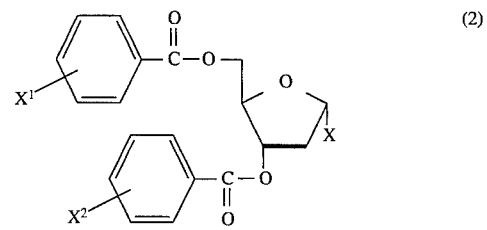

(wherein X represents a halogen atom, and $X^1$ and $X^2$, the same or different, represent hydrogen or a halogen atom) in chloroform solvent in the presence of fluoride ion and in the presence of a copper compound as a catalyst.

2. A process for producing 5-trifluoromethyluracil comprising reacting 5-trifluoromethyl-5,6-dihydrouracil with alkylsulfoxide in the presence of a halogen and an acid catalyst.

3. The process according to claim 2, wherein said alkylsulfoxide is represented by the formula $R^1SOR^2$ (wherein $R^1$ and $R^2$, the same or different, represent $C_1$–$C_4$ alkyl).

4. The process according to claim 2, wherein said acid catalyst is selected from the group consisting of trifluoroacetic acid, camphor sulfonic acid, p-toluenesulfonic acid, trimethylsilane chloride, phosphorus pentoxide, sulfuric acid and hydrochloric acid.

5. The process according to claim 2, wherein said halogen is selected from the group consisting of $I_2$, $Br_2$ and ClI.

6. A process for producing 1-(2'-deoxy-β-D-erythro-pentofuranosyl)-5-trifluoromethyluracil of the formula (3):

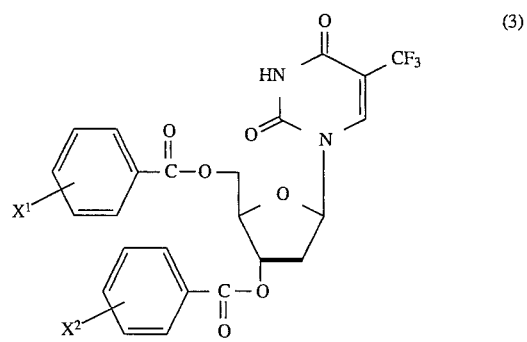

comprising reacting 5-trifluoromethyl-2,4-bis(trimethylsilyloxy)pyrimidine of the formula (1)

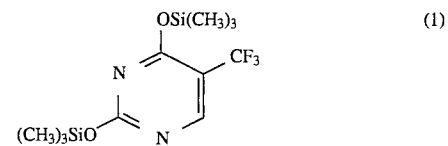

with 2-deoxy-α-D-erythro-pentofuranosyl halide derivative of the formula (2)

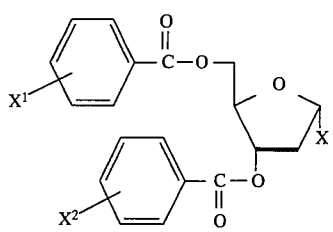

(2)

(wherein X represents a halogen atom, and $X^1$ and $X^2$, the same or different, represent hydrogen or a halogen atom) in chloroform solvent in the presence of fluoride ion and in the presence of a copper compound as a catalyst.

7. The process according to claim 6, wherein said X, $X^1$ and $X^2$ represent chlorine atom.

8. The process according to claim 6, wherein said copper compound is selected from the group consisting of cupric chloride and copper fluoride.

* * * * *